(12) United States Patent
Nudo, Sr.

(10) Patent No.: US 6,997,191 B2
(45) Date of Patent: Feb. 14, 2006

(54) DENTAL CLEANING TOOL

(76) Inventor: Alexander S. Nudo, Sr., 1725 Wiggins Ave., Springfield, IL (US) 62704

( * ) Notice: Subject to any disclaimer, the term of this patent is extended or adjusted under 35 U.S.C. 154(b) by 565 days.

(21) Appl. No.: 10/337,728

(22) Filed: Jan. 8, 2003

(65) Prior Publication Data

US 2003/0140939 A1 Jul. 31, 2003

Related U.S. Application Data

(60) Provisional application No. 60/352,289, filed on Jan. 30, 2002.

(51) Int. Cl.
*A61C 15/00* (2006.01)

(52) U.S. Cl. .................................... 132/328; 132/325
(58) Field of Classification Search .......... 132/323–327, 132/328
See application file for complete search history.

(56) References Cited

U.S. PATENT DOCUMENTS

| | | | | |
|---|---|---|---|---|
| 664,126 | A | * 12/1900 | Cowan | 132/325 |
| 1,507,313 | A | * 9/1924 | Hudson | 132/326 |
| 1,882,204 | A | * 10/1932 | Zrna | 132/323 |
| 3,311,116 | A | 3/1967 | Foster | 132/326 |
| D237,086 | S | 10/1975 | Gore | D28/68 |
| D285,368 | S | 8/1986 | Morin et al. | D28/68 |
| 5,052,420 | A | 10/1991 | Chen | 132/325 |
| 5,246,022 | A | 9/1993 | Israel et al. | |
| 5,279,314 | A | 1/1994 | Poulos et al. | |
| 5,375,615 | A | 12/1994 | Wahlstrom | |
| 5,415,187 | A | 5/1995 | Heneveld | |
| 5,423,427 | A | * 6/1995 | Brown | 206/581 |
| 5,560,378 | A | 10/1996 | Tiphonnet | 132/325 |
| 5,566,872 | A | 10/1996 | Dolan et al. | |
| 5,607,050 | A | 3/1997 | Dolan et al. | |
| 5,647,385 | A | 7/1997 | Zebuhr | |
| 5,749,380 | A | 5/1998 | Zebuhr | |
| 5,769,102 | A | 6/1998 | Zebuhr | |
| 5,782,250 | A | * 7/1998 | Harrah, Jr. | 132/327 |
| 5,860,435 | A | 1/1999 | Hippensteel | |
| D413,695 | S | 9/1999 | Bitz | D28/66 |
| 6,006,762 | A | 12/1999 | Hsia | |
| 6,047,712 | A | 4/2000 | Blades | |
| 6,123,087 | A | 9/2000 | Jang | 132/325 |
| 6,131,586 | A | 10/2000 | Flanagan | |
| 6,189,545 | B1 | 2/2001 | Tamez | |
| 6,220,256 | B1 | 4/2001 | Dolan et al. | |
| 6,363,949 | B1 | 4/2002 | Brown | |
| 6,571,804 | B1 | * 6/2003 | Adler | 132/325 |

\* cited by examiner

*Primary Examiner*—Kevin Shaver
*Assistant Examiner*—Stephanie L. Willatt

(57) ABSTRACT

A pocket carried dental floss dispensing and cleaning device is provided to permit a user to open the device for use and close the device to secure the tool in a sanitary environment. A spool of dental floss is contained within a pivoting floss support arm removeably mounted a storage compartment. A knob is used to open the device and secure a line of floss during use.

15 Claims, 5 Drawing Sheets

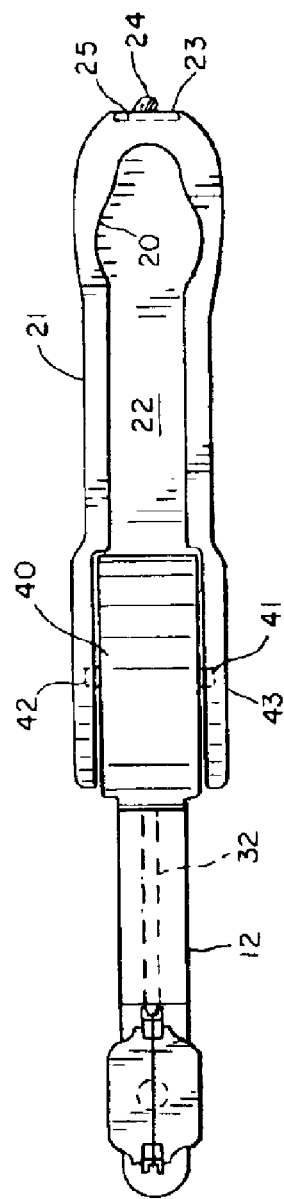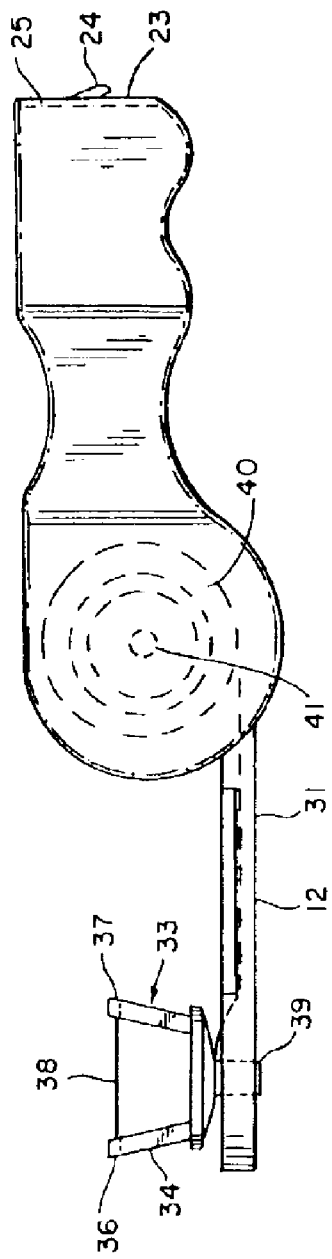

DENTAL CLEANING TOOL

RELATED APPLICATIONS

The present application is related to U.S. Provisional application Ser. No. 60/352,289 filed Jan. 30, 2002.

FIELD OF THE INVENTION

The present invention relates to a portable tooth and gum cleaning device including a dental floss dispenser, and in particular to a modular tooth and gum cleaning device having nesting top and bottom portions which pivot into an open position for use.

BACKGROUND OF THE INVENTION

Dentists professionally insist now that their patients floss their teeth at least three times a day or after every meal. The most popular of dental floss dispensers provides a reel of dental floss in a rectangular package and a cutter for cutting a line of dental floss. The top of the package and the cutting blade are protected by a hinged lid. Unfortunately, this form of dispensing does not provide a user with a tool for reaching into the back of the mouth. The user is forced to wash up and use their fingers to find the hidden areas in the teeth.

Although prior art flossing dispensers have addressed many of the problems in reaching to the rear teeth, most designs are awkward and fail to fit comfortable in the user's pocket. The elongated designs which are constructed to reach the rear of the user's mouth often break in the user's pocket. The flossing dispenser designs with flossing bridges break off posts which make the flossing action impossible.

Hundreds of patents have issued over the years on dental floss tools designed to overcome these problems. Dental floss dispensers are illustrated and described in U.S. Pat. Nos. 5,375,615, 5,860,435, 6,006,762, 6,131,586, 6,363,949. Unfortunately, these concepts have failed to provide the public with a successful tool for reaching far into the mouth because the floss becomes lodged into the dispensing feed of the dispenser. Although most people today still use the old plastic floss dispenser, there is still a need for a portable dental floss cleaning and dispensing tool that can be carried in a pocket of a shirt or pants.

SUMMARY OF THE INVENTION

In accordance with the present invention, a pocket carried dental floss dispensing and cleaning device is provided to permit a user to open the device for use and close the device to secure the tool in a sanitary environment.

It is an object of the present invention to provide a tooth and gum cleaning device containing a spool of dental floss for dispensing dental floss to a pivoting floss support.

It is another object of the present invention to provide a flossing device containing a spool of dental floss and an arm connected to a pivoting floss support, the arm further providing means for opening the device and securing a line of dental floss.

It is yet another object of the present invention to provide a flossing device having pivoting guide operable to guide said line of dental floss in a channel on the arm and onto flossing support posts.

DETAILED DESCRIPTION OF THE DRAWINGS

FIG. 4 is a top perspective view of a teeth and gum and cleaning device of the present invention with the top portion in the open position and guide in the closed position.

FIG. 6 is a side perspective view of a teeth and gum cleaning device of the present invention with a top portion and guide in the open position.

DETAILED DESCRIPTION

Figure 1:
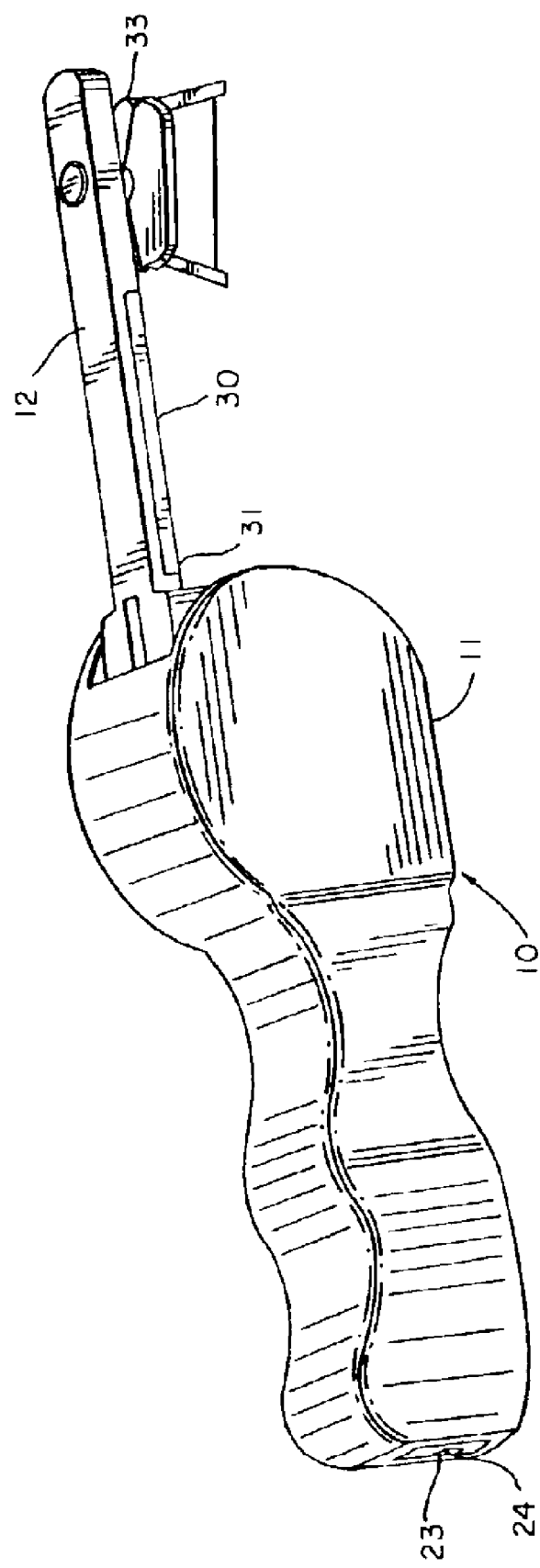
FIG. 1 is a perspective view of a teeth and gum cleaning device of the present invention.
Figure 2:
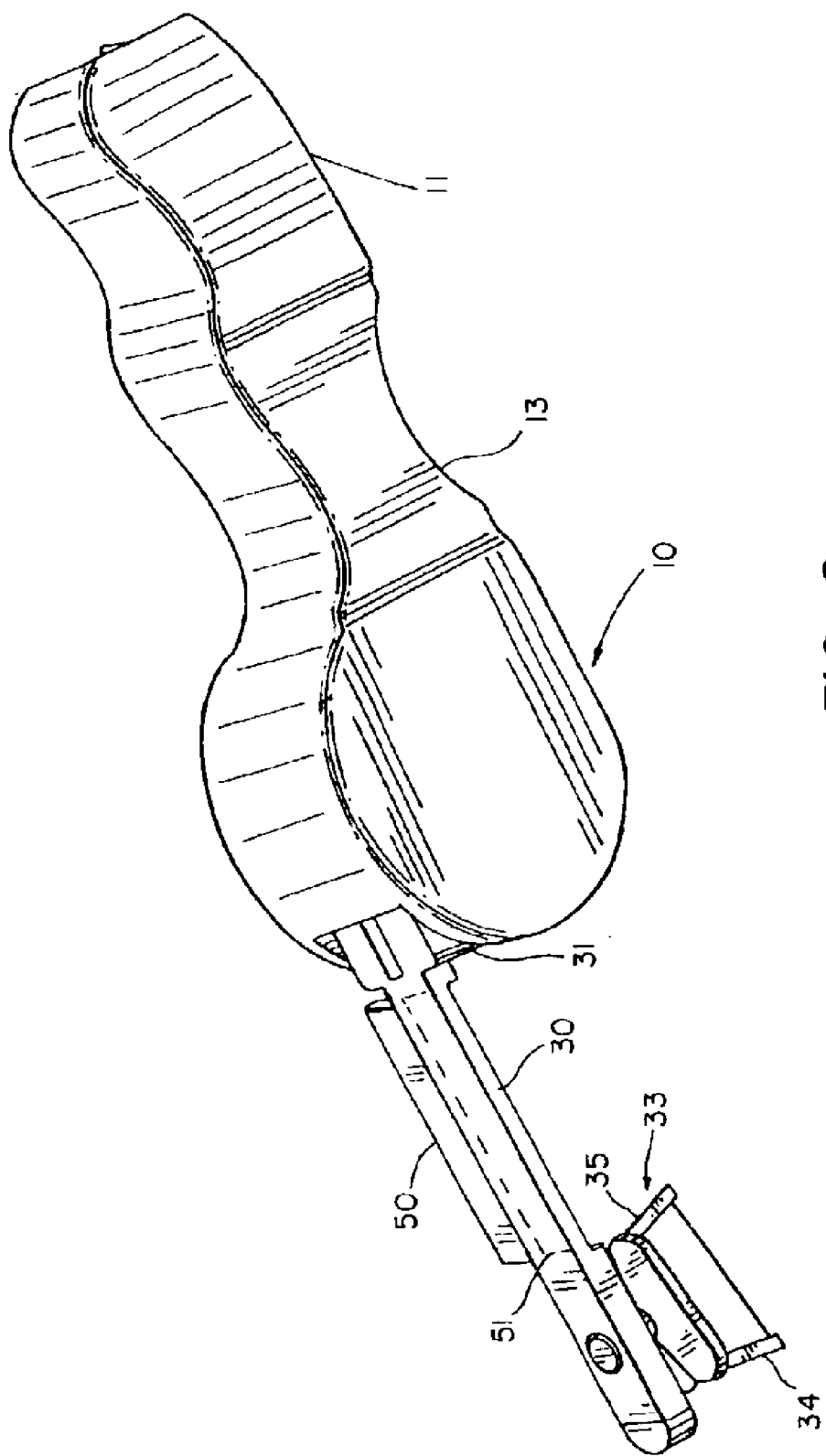
FIG. 2 is a perspective view of the teeth and gum cleaning device of the present invention with a top portion and guide in the open position.
Figure 3:
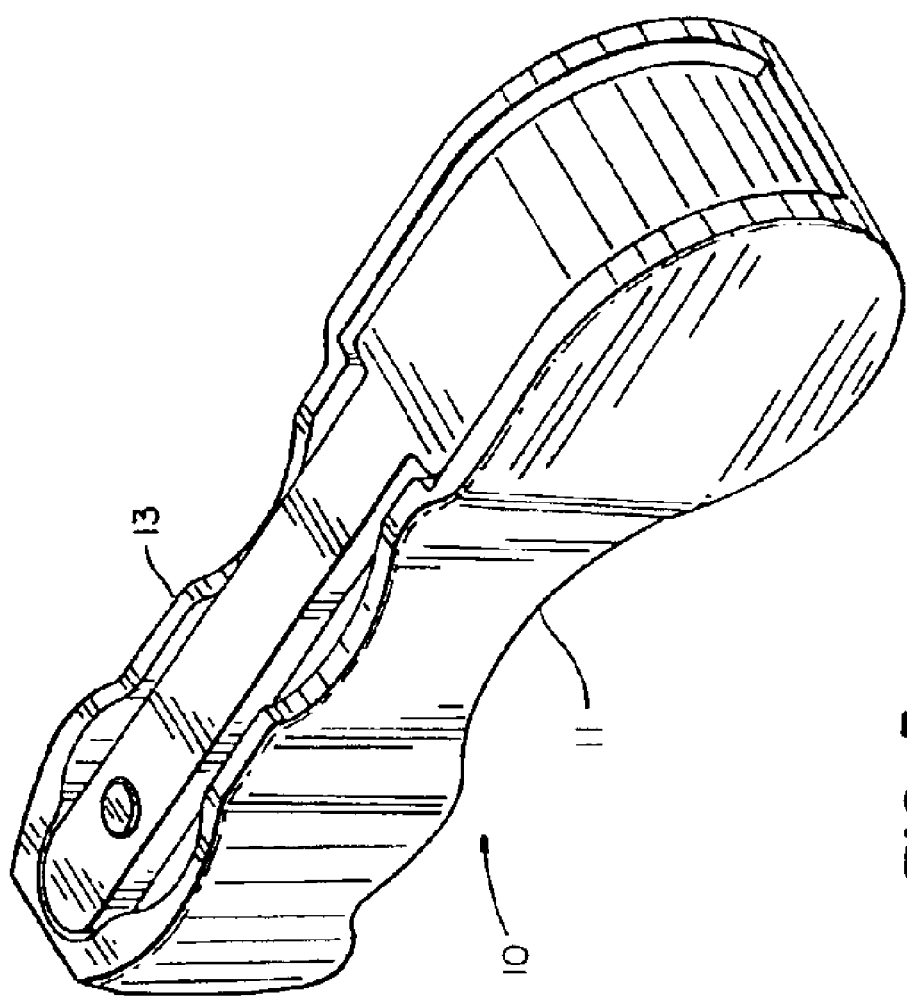
FIG. 3 is a perspective view of the teeth and gum cleaning device of the present invention with a top portion and guide in the closed position.
Figure 5:
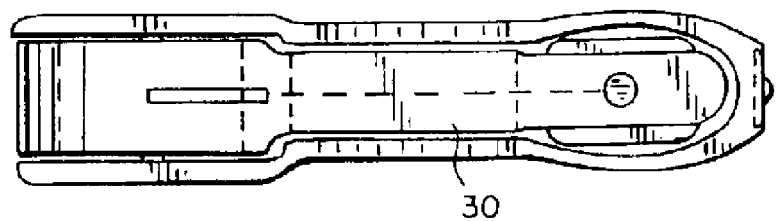
FIG. 5 is a bottom perspective view of a teeth and gum cleaning device of the present invention with a top portion and guide in the closed position.
Figure 7:
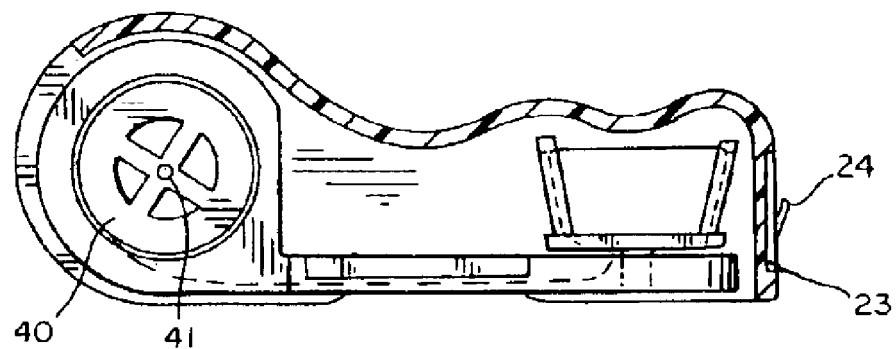
FIG. 7 is a perspective view of a teeth and gum cleaning device of the present invention with a top portion and guide in the closed position.
Figure 8:
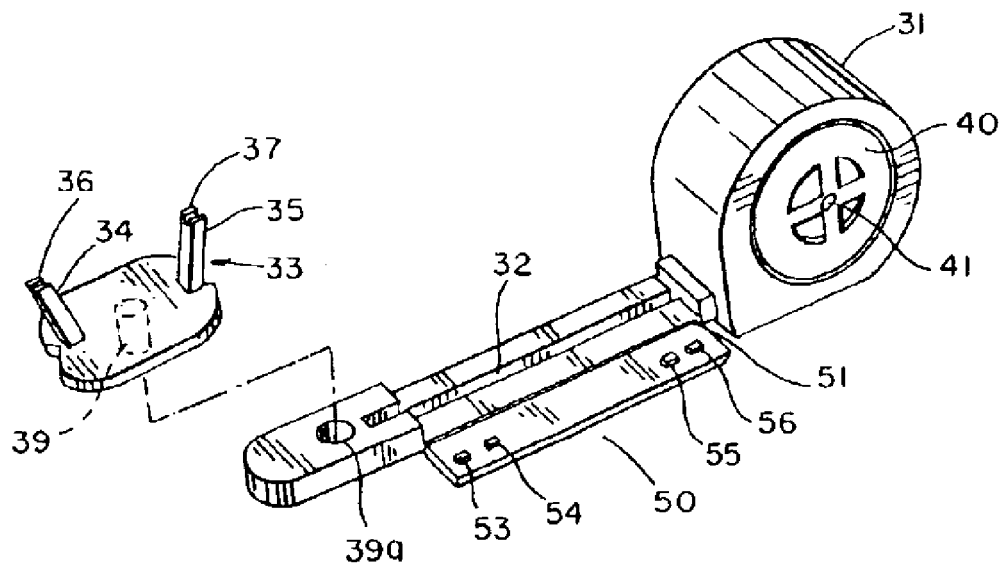
FIG. 8 is an explosive perspective view of floss support and cleaning device of the present invention with the guide in the open position.

Although the details of the present invention are shown in the drawings and described in the application, it is to be understood that the disclosed embodiments are merely exemplary of the invention, which may be embodied in various forms. Therefore, specific structure and functional details described herein are not to be interpreted as limiting, but merely as a basis for the claims and as a representative basis for the claims. Likewise, some parts of the invention as described in detail are engineered in precise design to form a unique structure which is the invention as claimed.

With reference now to the drawings, and in particular to FIGS. 1–8 thereof, a new and improved pocket carried dental floss dispenser or dental floss dispensing and cleaning device embodying the principles and concepts of the present invention and generally designated by the reference number 10 will be described. The device is made of plastic material which may be opaque or translucent or transparent. The plastic may also be a colored material such as blue or green or yellow. Embedded or coated on the plastic material may be an antimicrobial material such that the floss may disinfect the gum area by the antimicrobial material which is added to the floss as the floss travels through the dispenser. The antimicrobial material may be coated onto only the parts of the device which contact the floss. Well known antimicrobial material for use in plastics includes silver sulfates or biguanides.

A tooth and gum cleaning device 10 is shown in detail in FIGS. 1–8 and will be described with respect to all of the drawings. In FIG. 1, the tooth and gum cleaning device 10 includes a dispenser 10a having a housing 11 which utilizes a pivoting top cover portion 12 which pivots into an open position for use from a bottom base portion 13. The base portion 13 has an undercut 13a which conforms to a user's hand. The dispenser is about five inches in length and designed so the user can carry the device in the pants or shirt pocket. When it is necessary to use the dispenser, the user can quickly remove it from the pocket and return it. Moreover, the top portion 12 provides a flip open extension dispenser that permits the user to reach far into the mouth to clean the gums and teeth and eliminates the problems that occur when someone attempts to floss with both hands. As further shown in FIG. 1, the device is modular in design to ergonomically conform to a user's hand for easier use. The modular shape further permits the dispenser to be carried in the pocket comfortably without breaking.

As shown in FIG. 4, the base portion 13 has an inner wall 20 and an outer wall 21. The inner wall 20 and floor portion 20a define a trough or storage compartment 22. The storage compartment 22 houses the top cover portion 12 during nonuse in a nesting fit. The top portion 12 pivots back and into the storage chamber. The base portion 13 further includes a rear outer wall end 23 which houses a cutter 24. The cutter 24 is inserted into a slot 25 formed integrally with the base portion 13.

The top cover portion 12 includes an arm 30 and a pivoting floss support 31. The arm has a channel 32, a flossing bridge 33, a first floss support post 34 and a second floss support post 35. Each support post 34, 35 have a v-shaped groove 36, 37 for receiving a line of dental floss 38. The flossing bridge is pivotally mounted on the arm 30 by a stem 39 which extends though an aperture 39a in the arm 30. The stem 39 is pivotally mounted in the aperture by an interference fit or may be riveted into the aperture by any well known method. The top cover portion 12 is pivotally mounted inside the base portion 13 so that the top cover portion 12 may rotate to fit inside the base portion 13 during nonuse. The top portion 12 nests inside the base portion 13 to present a flush surface design.

The pivoting floss support 31 houses a reel of dental floss 40. The pivoting floss support 31 and the spool of dental floss 40 are removable and pivotally mounted on an axle 41 in the storage compartment. The axle 41 is loosely mounted in slots 42, 43 of the storage compartment so that the spool of dental floss may be removed at any time. The axle 41 also permits the arm 30 to pivot open for use.

Also mounted on the arm 31 is a pivoting guide means 50 for guiding the floss line 38 in the arm 30 through channel 32. The pivoting guide means includes a flap 50a which is connected to the arm 30 by a living hinge 51 which may be opened to position the line of floss 38 in channel 32 and closed to secure the line of floss in the channel. The flap 50 has a series of connecting extensions 53, 54, 55, and 56 which snap into channel 32 to secure the flap 50a in closed position and ready for use. The extensions 53–56 by extending into the channel 32 further serve the purpose of securing the line of floss inside the channel 32 while making contact with the floss to treat the floss with the antimicrobial material embedded in the plastic material.

In order to operate the pocket dispenser, the user removes the dispenser from the pocket and pivots open the arm 30. The guide 50 is pivoted thorough the hinge 51 to the open position and the line of floss is placed into the channel 32. The guide is then closed to lock the floss into the channel 32. As the line of floss 38 is further pulled out of the reel, the line is then positioned into the v-shaped grooves on each post and extended back to cutter where any extra line is cut. Any remaining extra floss is wrapped around stem 39 and the pocket floss is ready for use. After flossing, the used portion of the line is cut and the top cover portion is pivoted into the base portion.

I claim:

1. A teeth and gum cleaning device, said device having housing for dispensing a line of dental floss, said device comprising, a top portion and a bottom portion, said bottom portion having a storage compartment for housing said top portion in nesting relationship while in a closed position, said top portion pivotally connected to said bottom portion and operable to pivot to an open position in order to clean the teeth and gums of the user, said top portion further having an arm including a channel, a guide means for securing said line of floss in said channel, a pivoting flossing bridge for securing said line of dental floss for cleaning the teeth and gums of a user, and a removable reel of dental floss for dispensing said line of dental floss.

2. The teeth and gum cleaning device as recited in claim 1, said device having a housing made of antimicrobial material.

3. The teeth and gum cleaning device as recited in claim 1, said device having a housing made of plastic embedded with antimicrobial material.

4. The teeth and gum cleaning device as recited in claim 1, said device having a cutter mounted on said base portion.

5. The teeth and gum cleaning device as recited in claim 1, said guide means having a flap with a living hinge for connecting said flap to said arm.

6. The teeth and gum cleaning device as recited in claim 5, said flap having extensions for closing and securing said flap over said channel.

7. The teeth and gum cleaning device as recited in claim 1 said base portion having an undercut for gripping said device.

8. The teeth and gum cleaning device as recited in claim 1, said device having a housing made of colored plastic material.

9. A teeth and gum cleaning device, said device having housing for dispensing a line of dental floss, said device comprising, a top portion and a bottom portion, said bottom portion having a storage compartment for housing said top portion in nesting relationship while in a closed position, said top portion pivotally connected to said bottom portion and operable to pivot to an open position in order to clean the teeth and gums of the user, said top portion further having a channel, a pivoting flap for securing said line of floss in said channel, a flossing bridge for securing said line of dental floss for cleaning the teeth and gums of a user, and a removable reel of dental floss for dispensing said line of dental floss.

10. The teeth and gum cleaning device as recited in claim 9, said device having a housing made of antimicrobial material.

11. The teeth and gum cleaning device as recited in claim 9, said device having a flap provided with extensions made of plastic embedded with antimicrobial material for contacting said line of dental floss as the line of dental floss moves through said channel.

12. The teeth and gum cleaning device as recited in claim 9, said device having a cutter mounted on said base portion.

13. The teeth and gum cleaning device as recited in claim 9, said guide means having a flap with a living hinge for connecting said flap to said arm.

14. The teeth and gum cleaning device as recited in claim 9, said flap having extensions for closing and securing said flap over said channel.

15. The teeth and gum cleaning device as recited in claim 9 said base portion having and undercut for gripping said device.

* * * * *